(12) United States Patent
Wong et al.

(10) Patent No.: US 6,369,116 B1
(45) Date of Patent: Apr. 9, 2002

(54) COMPOSITION AND METHOD FOR TREATING GLAUCOMA

(75) Inventors: Vernon Wong, Menlo Park; Lin Peng, San Jose, both of CA (US)

(73) Assignee: Oculex Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/221,002

(22) Filed: Dec. 23, 1998

Related U.S. Application Data

(63) Continuation of application No. 09/160,635, filed on Sep. 24, 1998, which is a continuation of application No. 08/459,134, filed on Jun. 2, 1995, now Pat. No. 5,869,079.

(51) Int. Cl.$^7$ .............................................. A01N 43/38
(52) U.S. Cl. ........................ 514/913; 424/486; 424/488
(58) Field of Search .............................. 424/484, 486, 424/488; 514/944, 913

(56) References Cited

U.S. PATENT DOCUMENTS

| | | | |
|---|---|---|---|
| 4,478,818 A | | 10/1984 | Shell et al. .................... 424/14 |
| 4,863,457 A | * | 9/1989 | Lee |
| 4,865,846 A | * | 9/1989 | Kaufman |
| 4,997,652 A | | 3/1991 | Wong ......................... 424/428 |
| 5,075,115 A | | 12/1991 | Brine ......................... 424/486 |
| 5,164,188 A | | 11/1992 | Wong ......................... 424/428 |
| 5,268,178 A | * | 12/1993 | Calhoun et al. |
| 5,356,629 A | | 10/1994 | Sander et al. ............... 424/422 |
| 5,385,887 A | | 1/1995 | Yim et al. .................... 514/12 |
| 5,501,856 A | | 3/1996 | Ohtori et al. ............... 424/428 |
| 5,656,297 A | * | 8/1997 | Bernstein et al. |
| 5,707,643 A | * | 1/1998 | Ogura |

OTHER PUBLICATIONS

R. Baker, "Controlled Release of Biologically Active Agents," *A Wiley–Interscience Publication*, p. 73 (1987).
G. DiColo, "Controlled drug release from implantable matrices based on hydrophobic polymers," *Biomaterials* 1992, vol. 13, No. 12:850–853.
T. Jackanicz et al, "Polylactic Acid As A Biodegradable Carrier For Contraceptive Steroids," *Contraception*, vol. 8, No. 3:227–235.
R. Miller et al, "Degradation Rates of Oral Resorbable Implants (Polylactates and Polyglycolates): Rate Modification with Changes in PLA/PGA Copolymer Ratios," *J. Biomed. Mater. Res.*, vol. 11:711–719 (1977).
J. Heller, "Biodegradable Polymers in Controlled Drug Delivery," *CRC Critical Reviews in Therapeutic Drug Carrier Systems*, vol. 1, Issue 1:39–90.
J. Charles, et al, "Use of Bioerodible Polymers Impregnated with Mitomycin in Glaucoma Filtration Surgery in Rabbits," *Ophthalmology*, Apr. 1991, vol. 98, No. 4: 503–508.
H. Jampel, et al, "Glaucoma Filtration Surgery in Monkeys Using 5–Fluorouridine in Polyanhydride Disks," *Arch Ophthalmol*, Mar. 1990, vol. 108:430–435.
D. Lee, et al, "The Use of Bioerodible Polymers and 5–Fluorouracil in Glaucoma Filtration Surgery," *Investigative Ophthalmology & Visual Science*, Nov. 1988, vol. 29, No. 11:1692–1697.
M. Chang, et al, "Basic Science and Clinical Aspects of Wound Healing in Glaucoma Filtering Surgery," *Journal of Ocular Pharmacology and Therapeutics*, 1998, vol. 14, No. 1:75–95.
D. Lee, et al, "Glaucoma Filtration Surgery in Rabbits Using Bioerodible Polymers and 5–Fluorouracil," *Ophthalomology*, Dec. 1987, vol. 94, No. 12:1523–1530.
T. Smith, et al, "Sustained–release subconjunctival 5–Fluorouracil," *Ophthalmic Surgery Lasers*, Sep. 1996, vol. 27, No. 9:763–767.

* cited by examiner

*Primary Examiner*—Edward J. Webman
(74) *Attorney, Agent, or Firm*—David J. Brezner; Todd A. Lorenz; Flehr Hohbach Test Albritton & Herbert LLP

(57) ABSTRACT

Implants and methods are provided for modulating wound healing and controlling infection to improve the success of glaucoma filtration surgery. Formulations of one or more therapeutically active agents and a biodegradable polymer provide a substantially constant rate of release for an extended period of time.

19 Claims, 5 Drawing Sheets

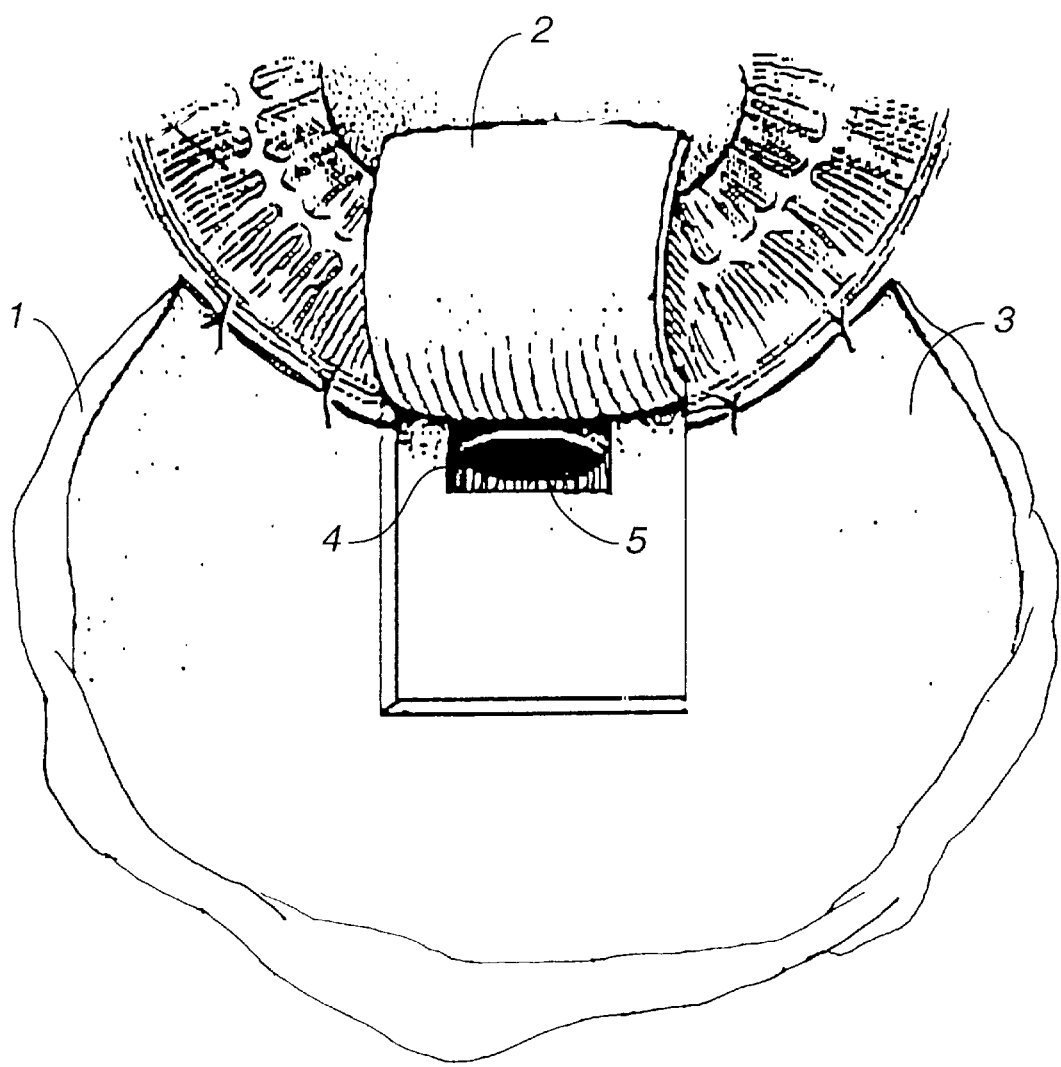
FIG._3

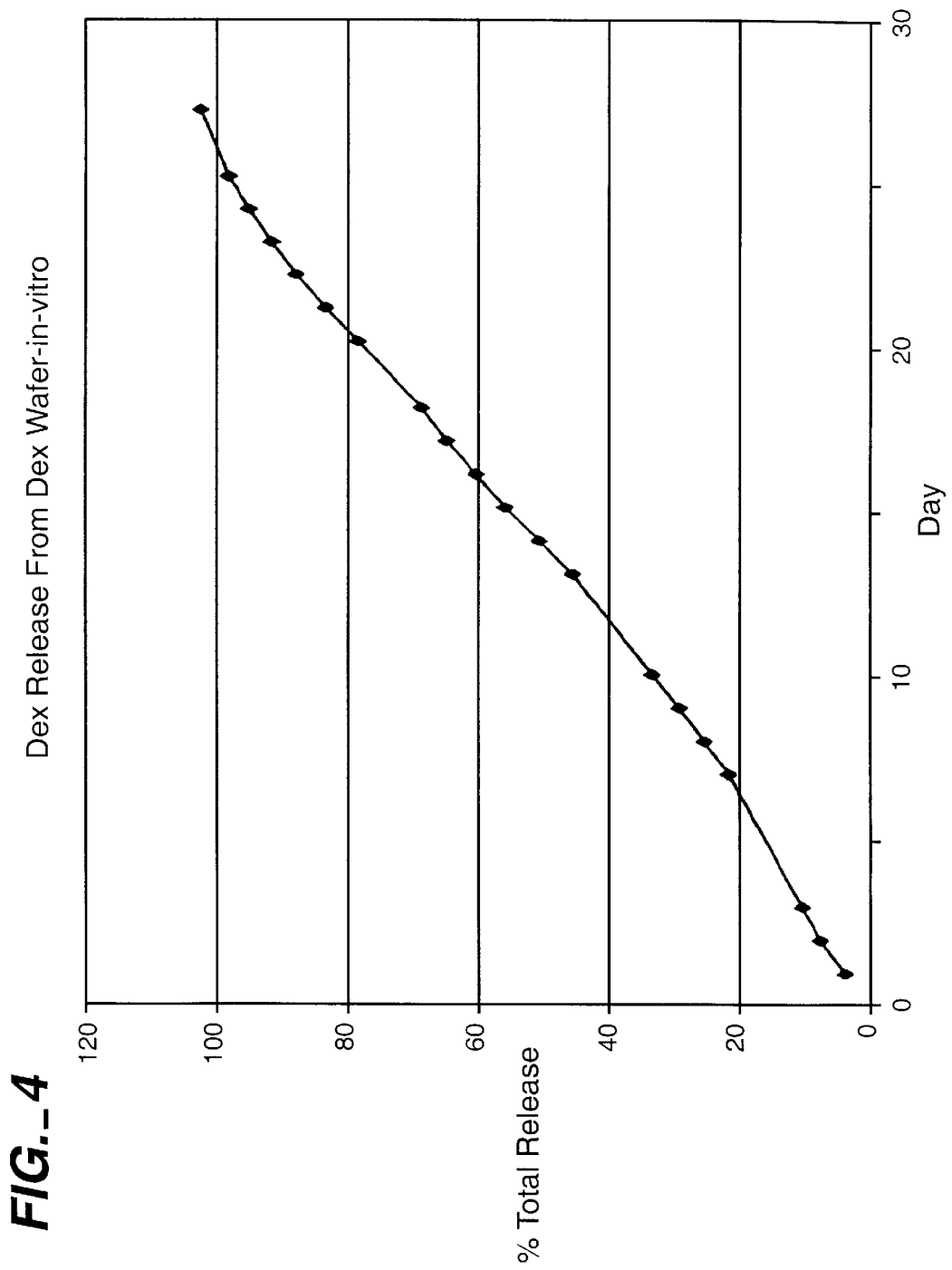
FIG._4

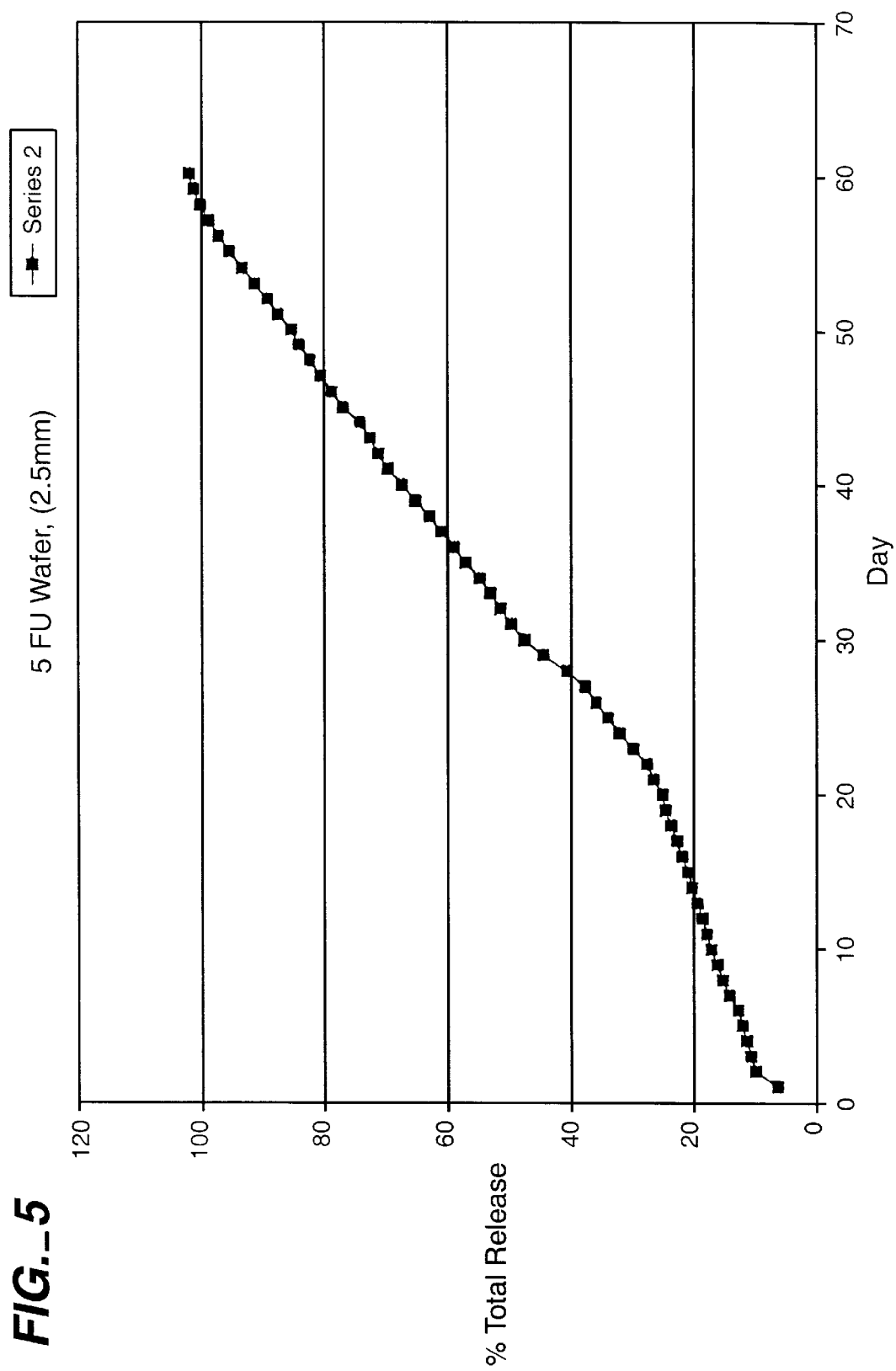
FIG._5

COMPOSITION AND METHOD FOR TREATING GLAUCOMA

This appln is a continuation of Ser. No. 09/160,635 filed Sep. 24, 1998 which is a continuation of Ser. No. 08/459,134 filed Jun. 2, 1995 U.S. Pat. No. 5,869,079.

TECHNICAL FIELD

The present invention relates to controlled-release biodegradable implants for use in glaucoma filtration surgery.

BACKGROUND OF THE INVENTION

Glaucoma filtration surgery (GFS) is the mainstay of surgical intervention for patients whose glaucoma remains progressive after medical therapy. In this procedure, a sclerectomy is performed to create a permanent fistula between the anterior chamber and the subconjunctival space. The procedure is designed to create a filtering bleb which provides an alternative passageway for the drainage of aqueous humor from the eye, thereby easing intraocular pressure and helping to improve the patient's vision.

Unfortunately, the failure rate of GFS can be as high as 25%, depending on preoperative risk factors, and even higher for more complicated cases. Shields, A Study Guide for Glaucoma, 2nd Edition, pp. 463–77 (Baltimore: Williams & Wilkins 1987). The most significant cause of these failures is the formation of excessive scar tissue by fibroblasts at the episcleral-conjunctival interface, which obstructs the release of fluid from the anterior chamber of the eye via the filtering bleb. Without the benefit of the alternative passageway created by the surgery, the intraocular pressure eventually returns to its pre-surgical elevated level.

Post-operative administration of a variety of therapeutically active agents has been investigated in the prior art to inhibit the inflammatory response, and in particular to help prevent fibroblast proliferation at the surgical site and the consequent formation of collagenous scar tissue. These include anti-inflammatory agents such as corticosteroids and non-steroidal anti-inflammatory drugs (NSAIDs), thrombolytic agents, antimetabolites and/or anti-proliferative agents. Chang, J. Ocular Pharm. Ther. 14:75–95 (1998). Typically, the desired active agent is administered via subconjunctival injection several times after the conclusion of GFS. The disadvantage of patient discomfort with these repeated subconjunctival injections, however, is obvious. Moreover, frequent subconjunctival injections of certain useful active agents such as 5-flourouracil (5-FU) can cause additional complications. Lee et al., Ophthalmic Surg 18:187 (1987).

Alternatively, a single subconjunctival injection of the desired active agent can be followed by topical eyedrops for up to three months post-operatively. This alternative procedure is equally unsatisfactory, however, since both the amount of active agent contacting the surgical site and the duration of exposure to the agent are very limited, typically resulting in bursts of drug delivery at each administration with nothing in between. Further, strict adherence to the eyedrop regime is crucial to the success of the procedure, and often neglected by many patients once beyond the constant oversight of medical professionals. Thus, a sustained- and controlled-release form of these active agents would be highly desirable.

Prior art attempts to formulate drug delivery systems suitable for the GFS procedure have failed to meet this need. Repeated investigations using bioerodible polyanhydride discs impregnated with 5-flourouracil (5-FU) achieved only limited success, had greatly varying release rates, and resulted in unacceptable ocular toxicity. Jampel, Arch. Ophthalmol. 108:430–435 (1990). Accordingly, a need still exists for an effective, pharmaceutically-acceptable implant which can provide both sustained and controlled release of the active agent directly to the surgical site.

Relevant Literature

U.S. Pat. No. 4,997,652 and 4,853,224 disclose biocompatible implants for introducing into an anterior chamber or posterior segment of an eye for the treatment of an ocular condition. U.S. Pat. Nos. 5,164,188, 5,443,505, 5,766,242 and 5,824,072 describe methods of treating ocular conditions by introduction of biocompatible implants comprising drugs of interest into the suprachoroidal space or pars plana of the eye. U.S. Pat. No. 5,501,856 describes biodegradable intra-ocular implants to be applied to the interior of the eye for treatment of disorders in retina/vitreous body or for glaucoma.

Heller, Biodegradable Polymers in Controlled Drug Delivery, in: CRC Critical Reviews in Therapeutic Drug Carrier Systems, Vol. 1, CRC Press, Boca Raton, Fla., 1987, pp. 39–90, describes encapsulation for controlled drug delivery. Heller in: Hydrogels in Medicine and Pharmacy, N.A. Peppes ed., Vol. III, CRC Press, Boca Raton, Fla., 1987, pp 137–149, further describes bioerodible polymers.

Anderson et al., Contraception 13:375 (1976) and Miller et al., J. Biomed. Materials Res. 11:711 (1977), describe various properties of poly(dL-lactic acid). U.S. Pat. No. 5,075,115 discloses sustained release formulations with lactic acid polymers and co-polymers. Di Colo, Biomaterials 13:850–856 (1992) describes controlled drug release from hydrophobic polymers.

Charles et al., Ophthalmology 98:503–508 (1991); Jampel et al., Arch. Ophthalmol. 108:430–435 (1990); Lee et al., Invest. Ophthalmol Vis. Sci. 29:1692–1697 (1988); and Lee et al., Ophthalmology 12:1523–1530 (1987) describe the use of bioerodible polyanhydride delivery systems in glaucoma filtration surgery. Smith and Ashton, Ophthalmic Surg. Lasers 27:763–767 (1996) describe a non-biodegradable reservoir system for delivery of 5-FU in high-risk glaucoma surgical patients.

SUMMARY OF THE INVENTION

Methods and compositions are provided for improving the success of glaucoma filtration surgery, through the sustained and controlled release of one or more therapeutically active agents directly to the surgical site. Biodegradable implants are provided comprising a biocompatible, biodegradable polymer and one or more active agents configured for placement extrinsic to the vitreous either episclerally or intrasclerally. The implant provides a substantially constant rate of release of the desired active agent or agents to the surgical site for an extended period of time.

BRIEF DESCRIPTION OF THE DRAWINGS

FIG. 3 is a front view of an eye illustrating the scleral flap and fistula created during glaucoma filtration surgery.

FIG. 4 shows the release profile of dexamethasone from a disc-shaped drug delivery system.

FIG. 5 shows the release profile of 5-flourouracil from a disc-shaped drug delivery system.

DESCRIPTION OF THE SPECIFIC EMBODIMENTS

Figure 1A:
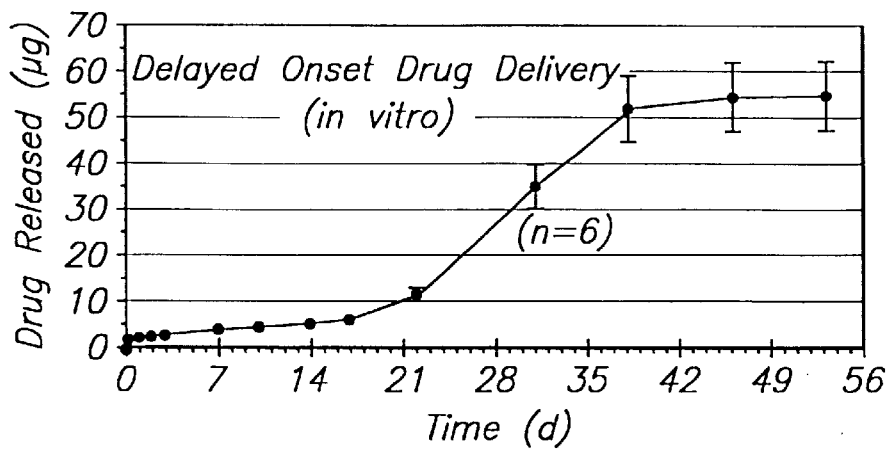
FIG. 1A shows the release profile of a hydrophobic drug from an extended release drug delivery system.

As shown herein, the success rate of GFS can be improved dramatically by the controlled and sustained administration of appropriate therapeutic agents to the episcleral-subconjunctival interface proximal to the surgical site, using an improved formulation of biodegradable implants. The implants comprise a pharmaceutically acceptable polymeric composition and are formulated to release one or more pharmaceutically active agents over an extended period of time and at a substantially constant rate of release, to provide a therapeutically effective dosage of the agent or agents directly to the surgical site to inhibit the inflammatory response. Thus, with a single administration therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

Pharmaceutically acceptable biodegradable polymeric compositions that may be employed in the implants of the present invention may be polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. In a particularly preferred embodiment, copolymers of glycolic and lactic acid are used, where the rate of biodegradation is controlled by the ratio of glycolic to lactic acid. The most rapidly degraded copolymer has roughly equal amounts of glycolic and lactic acid. Homopolymers, or copolymers having ratios other than equal, are more resistant to degradation.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In the preferred embodiment, the relative average molecular weight of the polymer will range from about 9 to about 60 kD, usually from about 10 to about 54 kD, more usually from about 12 to about 45 kD, and most preferably from about 15 to about 40 kD. The implant is formulated to release the active agent(s) over a period of at least about three weeks, more usually at least about four to six weeks, and usually not more than about one year, more usually not more than about three to six months. The formulation also provides for a substantially constant and uniform rate of release, which will usually not vary by more than about 100% over the desired period of time, more usually by not more than about 50%.

The release of drug from the implant can also be modulated by the addition of a release modulator. The release modulator is an agent that alters the release of a drug from a biodegradable implant in a defined manner. Release of a hydrophobic agent is increased by inclusion of an accelerator in the implant, while retardants are included to decrease the release rate of hydrophilic agents. Hydrophilic agents are those compounds which have at least about 100 µg/ml solubility in water at ambient temperature. Hydrophobic agents are those compounds which have less than about 100 µg/ml solubility in water at ambient temperature. The release modulator may be physiologically inert, or may also be a therapeutically active agent.

With this embodiment of the invention, the rate of release of the therapeutically active agent is controlled by the rate of transport through the polymeric matrix of the implant, and by the action of the modulator. The transport of drug through the polymer barrier is also affected by drug solubility, polymer hydrophilicity, extent of polymer cross-linking, expansion of the polymer upon water absorption so as to make the polymer barrier more permeable to the drug, geometry of the implant, and the like. At high drug loadings, i.e. at a loading concentration above the theoretical percolation threshold, percolation theory predicts the potential for drug leaching from the drug delivery system matrix. In such cases release modulators are useful to slow down the leaching process.

Active agents which may find use in the present invention to improve the post-operative success of glaucoma filtration surgery include, but are not limited to, the following therapeutic classes: Ace-inhibitor; endogenous cytokines that influence basement membrane; agents that influence growth of endothelial cells; adrenergic agonist or blocker; aldose reductose inhibitor; analgesic; anesthetic; antiallergic; antibacterial; antifibrotic; antifungal, e.g. amphoteracin B; antiglaucoma; antihyper- or hypotensive; anti-inflammatory; antineoplastic; antiprotozoal; antitumor; antimetabolites, e.g., folic acid analogs, purine analogs, and pyrimidine analogs; antiviral; carbonic anhydrase inhibitor; chelating agents; cholinergic; cholinesterase inhibitor; CNS stimulant; contraceptive; dopamine receptor agonist or antagonist; estrogen; glucocorticoid; glucosidase inhibitor; releasing factor; growth hormone inhibitor; growth stimulant; hemolytic; heparin antagonist; immunomodulator; immunosuppressant; LH-RH agonist; antimitotics; NSAID; anti-glaucoma agents, e.g acetozolamide (dimox), befunolol, β-blockers, Ca-blockers, etc.; anti-neoplastics, e.g., vinblastine, vincristine, interferons α, β, and γ; progesterone; thrombolytic; vasodilator; vasopressor; and vitamin.

Among hydrophobic drugs, which typically have a slow release profile and therefore benefit from formulation with a release accelerator, are cyclosporines, e.g. cyclosporin A, cyclosporin G, etc.; vinca alkaloids, e.g. vincristine and vinblastine; methotrexate; retinoic acid; certain antibiotics, e.g. ansamycins such as rifampin; nitrofurans such as nifuroxazide; non-steroidal anti-inflammatory drugs, e.g. diclofenac, ketorolac, flurbiprofen, naproxen, suprofen, ibuprofen, aspirin; etc. Steroids are of specific interest, in particular steroidal compounds with anti-inflammatory activity, i.e. glucocorticoids. Glucocorticoids include the following:

21-acetoxypregnenolone
alclometasone
algestone
amcinonide
beclomethasone
betamethasone
budesonide
chloroprednisone
clobetasol -continued clobetasone
cloprednol
clocortolone
corticosterone
cortisone
cortivazol
deffazacort
desonide
desoximetasone
dexamethasone
diflucortolone
diruprednate
enoxolone
fluazacort
flucloronide
flumethasone
flunisolide
fluocinolone acetonide
fluocinonide
fluocortinbutyl
fluocortolone
fluorometholone
fluperoloneacetate
fluprednidene acetate
fluprednisolone
flurandrenolide
formocortal
halcinonide
halometasone
halopredone acetate
hydrocortamate
diflorasone
hydrocortisone
hydrocortisone acetate
hydrocortisone phosphate
hydrocortisone 21-sodium succinate
hydrocortisone tebutate
mazipredone
medrysone
meprednisone
methylprednisolone
mometasone furoate
prednisolone sodium 21-m-sulfobenzoate
prednisolone 21-stearoylglycolate
prednisolone tebutate
prednisolone 21-trimethylacetate
prednisone
prednival
paramethasone
prednylidene
prednicarbate
prednylidene 21-diethylaminoacetate
prednisolone
prednisolone 21-diethylaminoacetate
tixocortol
triamcinolone
prednisolone sodium phosphate
triamcinolone acetonide
prednisolone sodium succinate
triamcinolone benetonide
triamcinolone hexacetonide.

These hydrocortisone derivatives have been recognized as having significant therapeutic effects that are beneficial in the treatment of ocular inflammatory diseases, varying in their potency and biotolerability as a function of their chemical substitutions.

The following are examples of glucocorticoids that have been used in the treatment of ocular inflammation, and are of interest for use in the subject invention: dexamethasone sodium phosphate; prednisolone sodium phosphate; prednisolone acetate; fluorometholone acetate; dexamethasone; fluoromethalone; and medrysone. Of these, dexamethasone is thought to be the most potent, and is therefore a good candidate for use in a GFS drug delivery system, because a small drug release rate is sufficient to establish therapeutic concentration levels at the surgical site.

Accelerators may be physiologically inert, water soluble polymers, e.g. low molecular weight methyl cellulose or hydroxypropyl methyl cellulose (HPMC); sugars, e.g monosaccharides such as fructose and glucose, disaccharides such as latose, sucrose, or polysaccharides, usually neutral or uncharged, such as cellulose, amylose, dextran, etc. Alternatively, the accelerator may be a physiologically active agent, allowing for a combined therapeutic formulation. The choice of accelerator in such a case will be determined by the desired combination of therapeutic activities.

Release retardants are hydrophobic compounds that slow the rate of release of hydrophilic drugs, allowing for a more extended release profile. Hydrophilic drugs of interest which may benefit from release modulation include water soluble antibiotics, e.g. aminoglycosides such as gentamycin, kanamycin, neomycin, and vancomycin; amphenicols such as chloramphenicol; cephalosporins such as cefazolin HCl; penicillins such as ampicillin, penicillin, carbenicillin, oxycillin, methicillin; lincosamides such as licomycin; polypeptide antibiotics such as polymixin and bacitracin; tetracyclines such as tetracycline; quinolones such as ciprofloxacin, etc.; sulfonamides such as chloramine T; and sulfones such as sulfanilic acid. Also of interest as active hydrophilic agents are nucleotide analogs, e.g. acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like.

Agents of interest as release retardants include non-water soluble polymers, e.g. high molecular weight methylcellulose and ethylcellulose, etc., low water soluble organic compounds, and pharmaceutically active hydrophobic agents, as previously described.

Co-delivery of therapeutic agents from two different therapeutic classes may be particularly beneficial for the post-operative care of GFS patients. Combinations of interest include anti-inflammatory and anti-proliferative, e.g. glucocorticoid and methotrexate, glucocorticoid and 5-fluorouracil, NSAID and methotrexate; anti-inflammatory and antiviral; e.g. glucocorticoid or NSAID in combination with vidarabine, azidothymidine, dideoxyinosine, dideoxycytosine, acyclovir, foscarnet, or gancyclovir; anti-inflammatory and antibacterial, e.g. glucocorticoid and quinolone, NSAID and quinolone. In a particularly preferred embodiment, the implant comprises dexamethasone and 5-flourouracil or dexamethasone and ciprofloxacin. Other more specific combinations of interest include the NSAID diclofenac combined with an antibacterial such as gentamicin or vancomycin.

Antibacterial drug classes that may be advantageously combined with a suitable anti-inflammatory to improve the post-operative success of GFS include: aminoglycosides, amphenicols, ansamycins, lactams, lincosamides, macrolides, polypeptides, tetracyclines, diaminopyrimidines, nitrofurans, quinolones and analogs, sulfonamides, sulfones, etc. Where one compound does not cover the range of the bacterial infection, products may combine several antibacterial drugs in one combination product. Examples of antibiotics useful in treating ocular infections include: chloramphenicol; polymyxin b, neomycin, gramicidin; neomycin; bacitracin; sulfacetamide sodium; gentamicin; tobramycin; trimethprim sulfate; erythromycin; vancomycin; tetracycline; and chlortetracycline. Of particular interest are the quinolones, which are very potent, broad spectrum antibiotics. The high activity of these drugs allows a therapeutic concentration to be reached at low levels of the drug. Examples include ciprofloxacin; norfloxacin; ofloxacin; enoxacin, lomefloxacin; fleroxacin; temafloxacin, tosufloxacin and perfloxacin.

Combinations of anti-inflammatory agents with antiviral drugs are also of interest. These include a number of water soluble nucleotide analogs, e.g. acyclovir, gancyclovir, vidarabine, azidothymidine, dideoxyinosine and dideoxycytosine.

A combined anti-inflammatory drug, and antibiotic or antiviral, may be further combined with an additional therapeutic agent. The additional agent may be an analgesic, e.g. codeine, morphine, keterolac, naproxen, etc., an anesthetic, e.g. lidocaine; b-adrenergic blocker or b-adrenergic agonist, e.g. ephidrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine. Antihelminthic agents, e.g. ivermectin and suramin sodium; antiamebic agents, e.g chloroquine and chlortetracycline; and antifungal agents, e.g. amphotericin, etc. may be co-formulated with an antibiotic and an anti-inflammatory drug. Immunosuppressants such as azathioprine, cyclosporine and mizoribine are also of interest in combinations.

The amount of active agent employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

Where a release modulator is included, the amount employed will be dependent on the desired release profile, the activity of the modulator, and on the release profile of the active agent in the absence of modulator. An agent that is released very slowly or very quickly will require relatively high amounts of the modulator. Generally, the modulator will be at least about 10, more usually at least about 20 weight percent of the implant, and usually not more than about 50, more usually not more than about 40 weight percent of the implant.

Where a combination of active agents is to be employed, the desired release profile of each active agent is determined. If necessary, a physiologically inert modulator is added to precisely control the release profile. The drug release will provide a therapeutic level of each active agent.

The exact proportion of modulator and active agent is empirically determined by formulating several implants having varying amounts of modulator. A USP approved method for dissolution or release test will be used to measure the rate of release (USP 23; NF 18 (1995) pp. 1790–1798). For example, using the infinite sink method, a weighed sample of the drug delivery device is added to a measured volume of a solution containing four parts by weight of ethanol and six parts by weight of deionized water, where the solution volume will be such that the drug concentration after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. The drug concentration after 1 h in the medium is indicative of the amount of free unencapsulated drug in the dose, while the time required for 90% drug to be released is related to the expected duration of action of the dose in vivo. Normally the release will be free of larger fluctuations from some average value which allows for a relatively uniform release.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window.

The implants may be substantially homogeneous as to composition and physical characteristics or heterogeneous. Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

Other agents may be employed in the formulation for a variety of purposes. For example, buffering agents and preservatives may be employed. Water soluble preservatives which may be employed include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition. Where the buffering agent or enhancer is hydrophilic, it may also act as a release accelerator, and will have a cumulative effect with other modulator(s). Similarly, a hydrophilic buffering agent may act as a release retardant.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3–10 mm×5–10 mm with a thickness of about 0.1–1.0 mm for ease of handling. Where fibers are employed, the fiber diameter will generally be in the range of about 0.05 to 3 mm and the fiber length will generally be in the range of about 0.5–10 mm. Spheres will be in the range of 2 $\mu$m to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation. In the methods of the present invention, wafers, rods and sheets are preferable for intrascleral or episcleral implantation.

In some situations mixtures of implants may be utilized employing the same or different pharmacological agents. In this way, a cocktail of release profiles, giving a biphasic or triphasic release with a single administration is achieved, where the pattern of release may be greatly varied.

Various techniques may be employed to produce the implants. Useful techniques include solvent evaporation methods, phase separation methods, interfacial methods, extrusion methods, molding methods, injection molding methods, heat press methods and the like. Specific methods are discussed in U.S. Pat. No. 4,997,652, herein incorporated by reference. In a preferred embodiment, extrusion methods are used to avoid the need for solvents in manufacturing. When using extrusion methods, the polymer and drug are chosen so as to be stable at the temperatures required for manufacturing, usually at least about 85° C.

Turning now to FIG. 3, a basic description of the surgical procedure is provided to better illustrate the sites for implantation in accordance with the methods of the present invention. The transparent conjunctiva 1 is cut and reflected forward and a superficial or partial-thickness scleral flap 2 formed in the sclera 3 of the eye. The area between the conjunctiva 1 and the sclera 3 represents the episcleral-conjunctival interface. A fistula or osteum 4 is created through the underlying sclera 3 to communicate with the anterior chamber 5, after which the scleral flap 2 is sutured closed over the osteum 4. Ideally, after scleral healing the osteum 4 provides for leakage of aqueous humor from the anterior chamber 5 to the subconjunctival space, thereby easing intraocular pressure and helping to improve the patient's vision.

As noted previously, a frequent complication arises due to the formation of excessive scar tissue at or near the surgical site, which can block the filtering mechanism and deprive the patient of the benefit of the procedure. According to one embodiment of the present invention, then, an implant comprising a therapeutically active agent as described above is placed intralammellarly or intrasclerally 6 and proximal to the surgical site beneath the partial-thickness scleral flap 2. The implant may be either completely or partially covered by the flap 2 once the flap 2 is sutured closed. In a preferred embodiment, the implant is placed so that the flap 2 partially covers the implant, which serves to secure the implant from migrating beneath the flap 2 after closure. Alternatively, the implant is placed episclerally and proximal to the surgical site, either next to or on top of the sutured partial-thickness scleral flap 2 and underneath the conjunctiva 1.

Experimental

The following examples serve to illustrate certain preferred embodiments and aspects of the invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); kg (kilograms); $\mu$g (micrograms); L (liters); ml (milliliters); $\mu$l (microliters); cm (centimeters); mm (millimeters); $\mu$m (micrometers); nm (nanometers); ° C. (degrees Centigrade); h (hours); min (minutes); sec (seconds); msec (milliseconds); kD (kiloDaltons); mmHg (millimeters of Mercury); IOP (intra-ocular pressure).

EXAMPLE 1

Manufacture and Testing of a Drug Delivery System with Dexamethasone

Release of the hydrophobic drug dexamethasone from an extended release drug delivery system was measured. The drug delivery system was made with dexamethasone and polylactic acid/polyglycolic acid copolymer. Dexamethasone powder and a powder of polylactic acid polyglycolic acid (PLGA) copolymer having a relative average molecular weight of 15–20 kD were mixed thoroughly at a ratio of 50/50. The well-mixed powder was filled into an extruder, and heated for 1 hour at 95° C., then extruded through a 20 gauge orifice. Six implants of approximately 100–120 $\mu$g were cut from the extruded filaments for drug release assessment.

Each individual implant was placed in a glass vial filled with receptor medium (9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, each of the glass vials was placed into a shaking water bath at 37° C. Samples were taken for HPLC analysis from each vial at defined time points. The HPLC method was as described in USP 23 (1995) pp. 1791–1798. The concentration values were used to calculate the cumulative release profiles. The release profile is shown in FIG. 1A. It is seen that drug release is very slow with this implant. Appreciable drug release begins in the fourth week after initiation, at approximately the time of polymer disintegration.

A second implant was manufactured as described above, except that varying concentrations of hydrophilic hydroxypropylmethylcellulose (HPMC) were included as a release modifier. The combinations of drug, polymer and HPMC shown in Table 1 were used.

TABLE 1

| Lot # | PLGA | HPMC | Dexamethasone | Total |
|-------|------|------|---------------|-------|
| XT014 | 3.5  | 1.5  | 5             | 10    |
| XT015 | 2    | 2    | 5             | 9     |
| XT013 | 1.5  | 1.5  | 5             | 8     |

Figure 1B:
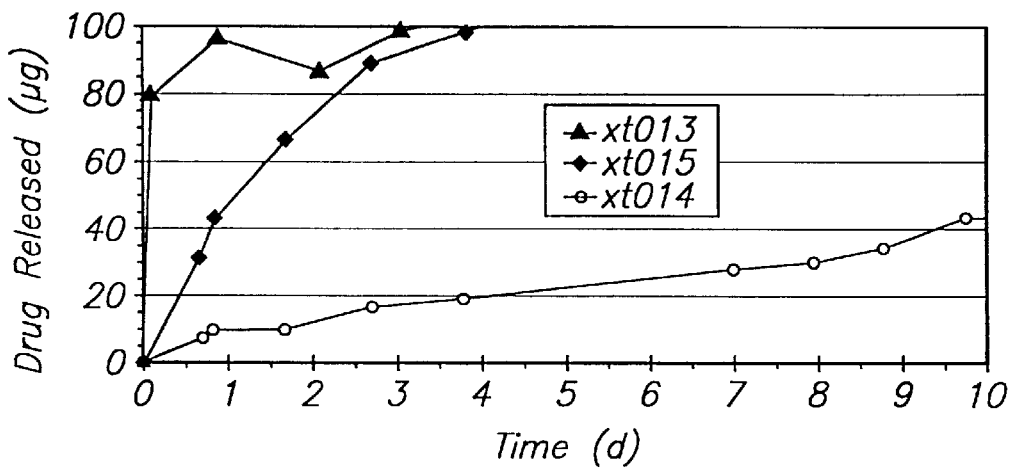
FIG. 1B shows the release profile of the same drug when formulated in a drug delivery system with a release modulator.

The release of drug was tested as described above. The data is shown in FIG. 1B. It is seen that with the addition of HPMC, there is a pronounced increase in the rate of release. Close to zero order release is observed for XT014 and XT015, where the ratio of release modulator to drug is 0.3 to 0.4. By selection of the appropriate polymer and release modifier, the drug release and delivery interval can be custom-tailored to provide a release profile that is accelerated or retarded.

EXAMPLE 2

Manufacture and Testing of a Drug Delivery System with a Pharmaceutically Active Release Modifier A drug delivery system was manufactured as described in Example 1, except that ciprofloxacin, a pharmaceutically active, hydrophilic compound, was included as the release modifier. The combinations of dexamethasone, polymer and ciprofloxacin shown in Table 2 were used.

TABLE 2

| Lot # | Release Modifier | PLGA | Drug |
|-------|------------------|------|------|
| XT029 | —                | 5    | 5 dexamethasone |
| XT032 | 2 ciprofloxacin  | 4    | 4 dexamethasone |
| XT030 | —                | 5    | 5 ciprofloxacin |

Figure 2A:
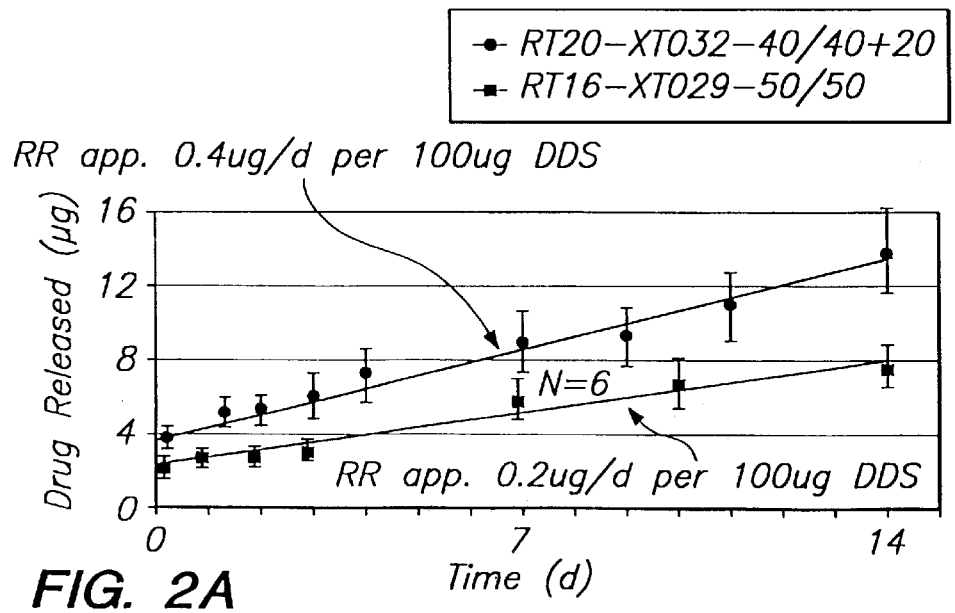
FIG. 2A shows the release profile of dexamethasone in the absence or presence of the release modifier, ciprofloxacin HCl.
Figure 2B:
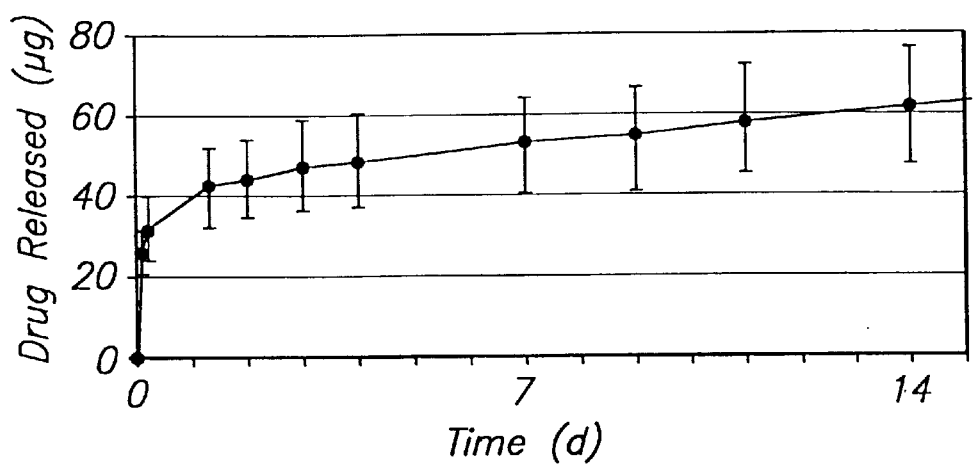
FIG. 2B shows the release of ciprofloxacin in the presence of dexamethasone.
Figure 2C:
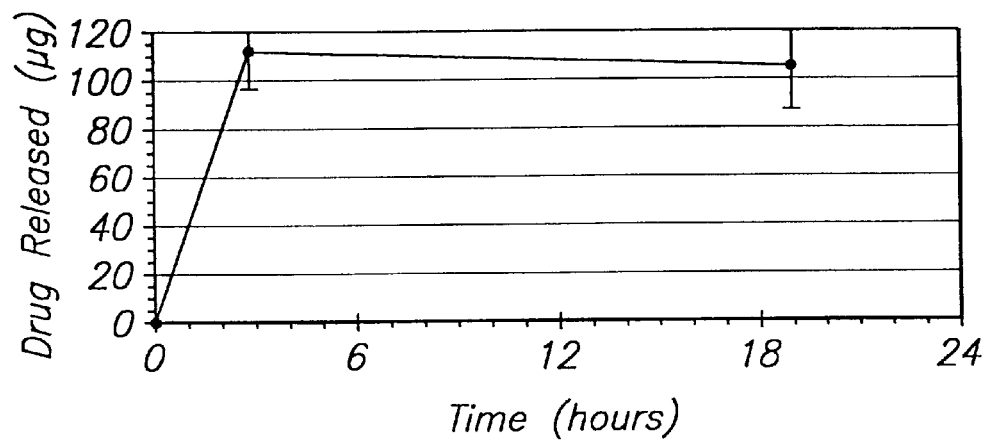
FIG. 2C shows the release of ciprofloxacin in the absence of a release modifier.

The release of dexamethasone is increased with the addition of ciprofloxacin, as shown by the data in FIG. 2A. The actual drug release is almost doubled when compared to the system without a modifier. In addition to the benefits of increased drug delivery, there are therapeutic benefits introduced with the antibiotic activity of ciprofloxacin. The release of ciprofloxacin from the same system is shown in FIG. 2B. The release rate is higher than that of dexamethasone. However, the overall release of ciprofloxacin is slower when co-formulated with dexamethasone than it is without dexamethasone, as shown in FIG. 2C.

EXAMPLE 3

Manufacture and Testing of a Drug Delivery System with Multiple Release Modifiers A drug delivery system was formulated with hydroxymethylcellulose, ciprofloxacin and dexamethasone, according to Table 3 below.

TABLE 3

| Lot # | PLGA | HPMC | Ciprofloxacin | Dexamethasone |
|---|---|---|---|---|
| XT035 | 3.4 | 0.4 | 2.4 | 3.8 |

Figure 2D:
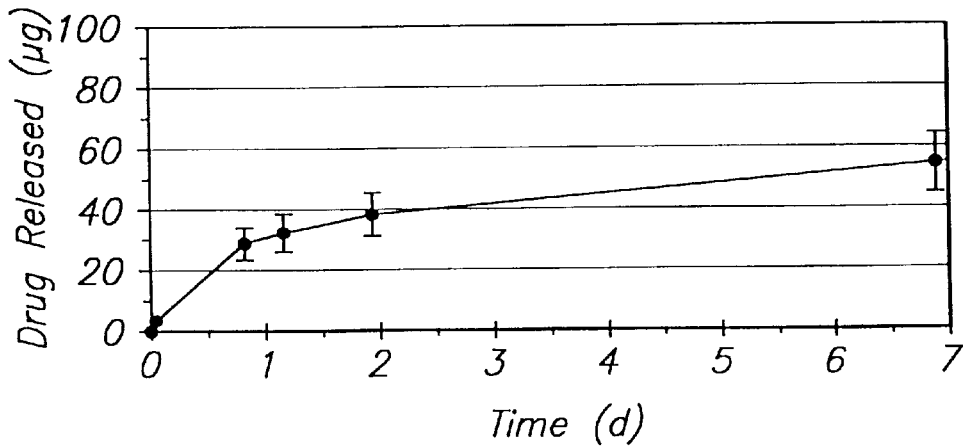
FIG. 2D shows the release profile from a drug delivery system having combined hydrophilic and hydrophobic drugs, and further having a pharmaceutically inactive release modifier.

The data in FIG. 2D show that after an initial higher release in the first day, an almost zero-order release thereafter can be observed. The overall release characteristic would be therapeutically acceptable from a therapeutic efficiency aspect.

EXAMPLE 4

Effect of Implant Geometry on Drug Release

A drug delivery system having a disc-shaped configuration was prepared with dexamethasone and polylactic acid/polyglycolic acid copolymer as described in Example 1 above, except that the implants comprised a 50:50 ratio of drug to polymer. The mixture of drug and PLGA was pressed into a sheet of pre-determined thickness, and wafers were cut to size with a trephine. The completed discs were approximately 2.5 mm in diameter and 0.15 to 0.16 mm thick.

The release of drug was tested as described in Example 1 above. As illustrated by the data in FIG. 4, in contrast to the rod-shaped system of Example 1 the disc-shaped DDS provided nearly zero-order release characteristics even without the incorporation of a release modifier. Thus, the geometry of the implant may also be varied to modify the release characteristics of the implant.

EXAMPLE 5

Post-Operative Use of Implants After Glaucoma Filtration Surgery

Implants comprising dexamethasone and a polylactic acid/polyglycolic acid copolymer were administered to patients undergoing glaucoma filtration surgery to control post-operative inflammation and to modulate wound healing. Implants of varying geometries were implanted episclerally and intrasclerally beneath a partial-thickness scleral flap. In the first study, a rod-shaped implant with and having HPMC as a release modifier (approximately 70:30 ratio of PLGA to HPMC) provided the following results:

TABLE 4

| Time | IOP mmHg (range) | n |
|---|---|---|
| Pre-op | 33.4 (28–38) | 5 |
| Day 1 | 7.2 (0–18) | 5[(1)] |
| Week 1 | 5.2 (0–14) | 5[(2)] |
| Week 3 | 8.4 (0–14) | 5[(3)] |
| Week 6 | 10.8 (8–17) | 4 |
| Month 3 | 10.5 (6–14) | 4 |
| Month 6 | 9.3 (6–12) | 3 |
| Month 12 | 5.3 (5–6) | 3[(4)] |

[(1)]one leak, one overfiltration;
[(2)]one CD; one overfiltration;
[(3)]one overfiltration;
[(4)]one cataract Similarly, a disc-shaped implant having 20% dexamethasone and no release modifier was implanted episclerally with the following results:

TABLE 5

| Time | IOP mmHg (range) | n |
|---|---|---|
| Pre-op | 31 (26–36) | 2 |
| Day 1 | 5 (3–7) | 2[1] |
| Week 1 | 8 (5–11) | 2[2] |
| Week 3 | 13 (8–18) | 2 |
| Week 6 | 13 (10–16) | 2 |
| Month 3 | 12 (9–17) | 2 |
| Month 6 | 15 (14–16) | 2 |
| Month 9 | 14 (14) | 1 |

[1]one overfiltration;
[2]one overfilitration.

As can be seen, in patients receiving the dexamethasone implants the intro-ocular pressure was maintained at levels significantly below the pre-surgical levels for an extended period of time.

EXAMPLE 6

Manufacture and Testing of a Mixed Polymer Implant with 5-Flourouracil

An implant having a disc-shaped configuration was prepared with 40% 5-flourouracil and a combination of two different molecular weight homo- and co-polymers. Polylactic acid having a molecular weight of approximately 40 kD was combined with polylactic acid/polyglycolic acid copolymer having a molecular weight of approximately 15 kD at a 2:3 ratio. The polymer/drug mixture was pressed into a sheet of pre-determined thickness, and wafers were cut to size with a trephine. The final measurements of the implants tested in this example were approximately 2.5 mm in diameter and approximately 0.15 to 0.16 mm thick.

The release of drug was tested as described in Example 1 above. As illustrated by the data in FIG. 5, this disc-shaped implant also provided near zero-order release of the active agent, 5-flourouracil, over an extended period of time.

EXAMPLE 7

Manufacture and Testing of an Implant with a Glucocorticoid and 5-Fluorouracil An implant is manufactured as described in Example 1, except that 5-fluorouracil, a pharmaceutically active, hydrophilic compound, is included as a release modifier. The combinations of drugs and polymer are as follows:

TABLE 6

| PLGA | Anti-tumor | Anti-Inflammatory |
| --- | --- | --- |
| 50% | — | 50% dexamethasone |
| 20% | 40% 5-fluorouracil | 40% dexamethasone |
| 40% | 20% 5-fluorouracil | 40% dexamethasone |
| 40% | 30% 5-fluorouracil | 30% dexamethasone |
| 50% | — | 50% 5-fluorouracil |

The release of dexamethasone is increased with the addition of 5-fluorouracil. In addition to the benefits of increased drug delivery, there are significant therapeutic benefits introduced with the antitumor activity of 5-fluorouracil. In particular, 5-FU has also proven to be effective in reducing fibroblast proliferation after glaucoma filtration surgery, and thus its combination with an anti-inflammatory agent will further enhance the long-term success of the procedure.

EXAMPLE 8

Manufacture and Testing of an Implant with a Glucocorticoid and Ganciclovir

An implant is manufactured as described in Example 1, except that ganciclovir, a pharmaceutically active, hydrophilic compound, is included as a release modifier. The combinations of drugs and polymer are as follows:

TABLE 7

| PLGA | Anti-Viral | Anti-Inflammatory |
| --- | --- | --- |
| 50% | — | 50% dexamethasone |
| 20% | 40% ganciclovir | 40% dexamethasone |
| 40% | 20% ganciclovir | 40% dexamethasone |
| 40% | 30% ganciclovir | 30% dexamethasone |
| 50% | — | 50% ganciclovir |

The release of dexamethasone is increased with the addition of ganciclovir. In addition to the benefits of increased drug delivery, there are therapeutic benefits introduced with the antiviral activity of ganciclovir.

EXAMPLE 9

Manufacture and Testing of an Implant with an NSAID and a Quinolone

An implant is manufactured as described in Example 1, combining the ciprofloxacin with the NSAID naproxen. The combinations of drugs and polymer are as follows:

TABLE 8

| PLGA | Quinolone | Anti-Inflammatory |
| --- | --- | --- |
| 50% | — | 50% naproxen |
| 20% | 40% ciprofloxacin | 40% naproxen |
| 40% | 20% ciprofloxacin | 40% naproxen |
| 40% | 30% ciprofloxacin | 30% naproxen |
| 50% | 50% ciprofloxacin | — |

The release of ciprofloxacin is decreased with the addition of naproxen. In addition to the benefits of increased drug delivery, there are therapeutic benefits introduced with the combined formulation.

It is evident from the above results that biodegradable implants formulated with an active agent and release modulator provide for release kinetics where the drug is released at a constant rate over long periods of time, avoiding the need of a patient to administer drugs in much less effective ways, such as topically. The implants provide an improved method of treating ocular and other conditions, by avoiding peaks and troughs of drug release. The implants find particular use in post-operative care of patients undergoing glaucoma filtration surgery, and can be used to delivery one or more therapeutically active agents to modulate wound healing and protect against infection.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for improving the post-operative success of glaucoma filtration surgery, said method comprising the steps of:
    introducing proximal to the surgical site an implant comprising dexamethasone at a concentration from about 40 to 80 weight percent of the implant and poly-lactate glycolic acid copolymer at a concentration of at least about 20 weight percent of the implant;
    wherein said therapeutically active agent is released within a therapeutic dosage which does not vary by more than about 100% for a period of at least about 3 weeks.

2. A method according to claim 1, wherein said implant further comprises a release modular.

3. A method according to claim 2, wherein said release modulator is a hydrophilic entity.

4. A method according to claim 2, wherein said release modulator is hydroxypropylmethylcellulose.

5. A method according to claim 2, wherein said release modulator is a therapeutically active agent.

6. A method according to claim 5, wherein said release modulator is a water soluble antibiotic.

7. A method according to claim 6, wherein said release modulator is ciprofloxacin.

8. A method according to claim 5, wherein said release modulator is an anti-proliferative agent.

9. An implant according to claim 8, wherein said release modulator is 5-fluorouracil.

10. A method according to claim 1, wherein said poly-lactate glycolic acid copolymer has a relative average molecular weight between about 10 and about 60 kD.

11. A method according to claim 1, wherein said implant is introduced intrasclerally beneath a partical-thickness scleral flap created during glaucoma filtration surgery.

12. A method according to claim 11, comprising the additional step of positioning said implant upon introduction beneath said partial-thickness scleral flap such that said flap partially covers said implant when closed.

13. A method according to claim 1, wherein said implant is introduced episclerally.

14. A method for improving the post-operative success of glaucoma filtration surgery, said method comprising the steps of:
    introducing proximal to the surgical site an implant comprising dexamethasone at a concentration from about 40 to 80 weight percent of the implant and a polylactate glycolic acid copolymer having a relative average molecular weight between about 10 and about 60 kD at a concentration of at least about 20 weight percent of the implant;

wherein said therapeutically active agent is released within a therapeutic dosage which does not vary by more than about 100% for a period of at least about 3 weeks.

15. A method according to claim 14, wherein said implant further comprises a release modulator.

16. A method according to claim 15, wherein said release modulator is a therapeutically active agent.

17. A method according to claim 16, wherein said release modulator is an anti-proliferative drug.

18. A method for improving the post-operative success of glaucoma filtration surgery, said method comprising the steps of:

introducing proximal to the surgical site an implant comprising a therapeutically active agent at a concentration from about 10 to 80 weight percent of the implant, hydroxypropylmethylcellulose at a concentration from about 10 to 50 weight percent of the implant, and at least one pharmacologically acceptable biodegradable polymer having a relative average molecular weight between about 10 and 60 kD at a concentration of at least about 20 weight percent of the implant;

wherein said therapeutically active agent is released within a therapeutic dosage which does not vary by more than about 100% for a period of at least about 3 weeks.

19. A method according to claim 18, wherein said pharmacologically acceptable biodegradabe polymer comprises a poly-lactate glycolic acid copolymer.

* * * * *